(12) United States Patent
Hugo

(10) Patent No.: US 6,267,594 B1
(45) Date of Patent: Jul. 31, 2001

(54) MEDICAL OR DENTAL-MEDICAL INSTRUMENT FOR MATERIAL-REMOVING WORKING OF BODY TISSUE AND TOOL FOR SUCH AN INSTRUMENT

(75) Inventor: Burkhard Hugo, Hettstadt (DE)

(73) Assignee: Kaltenbach & Voigt GmbH & Co., Biberach/Riss (DE)

( * ) Notice: Subject to any disclaimer, the term of this patent is extended or adjusted under 35 U.S.C. 154(b) by 0 days.

(21) Appl. No.: 09/315,837

(22) Filed: May 21, 1999

(30) Foreign Application Priority Data

Jun. 5, 1998 (DE) .............................. 198 25 261

(51) Int. Cl.$^7$ ................. A61C 1/07; A61C 3/06
(52) U.S. Cl. .................... 433/119; 433/125; 433/142
(58) Field of Search .................... 433/125, 118, 433/86, 119, 142, 143; 51/910, 162; 606/79, 82, 85

(56) References Cited

U.S. PATENT DOCUMENTS

| | | | | |
|---|---|---|---|---|
| 3,815,599 | * | 6/1974 | Deyrele | 606/82 |
| 4,069,824 | * | 1/1978 | Weinstock | 606/82 |
| 4,353,696 | * | 10/1982 | Bridges | 433/125 |
| 4,731,019 | * | 3/1988 | Martin | 433/125 |
| 4,954,082 | * | 9/1990 | Weisman | 433/125 |
| 5,092,875 | * | 3/1992 | McLees | 606/82 |
| 5,505,617 | * | 4/1996 | Steppmark et al. | 433/125 |
| 5,702,415 | * | 12/1997 | Matthai et al. | 606/82 |

FOREIGN PATENT DOCUMENTS

| | | | |
|---|---|---|---|
| 3908850 | * | 5/1990 | (DE) .................... 433/125 |
| 29509919 U1 | | 10/1995 | (DE) . |
| 19541032A1 | | 5/1997 | (DE) . |
| 74331 | * | 3/1983 | (EP) .................... 433/142 |
| 0106632A2 | | 4/1984 | (EP) . |
| 0360161A3 | | 3/1990 | (EP) . |
| 2639216 | * | 5/1990 | (FR) .................... 433/142 |
| 94/16640 | | 4/1994 | (WO) . |
| 96/14024 | | 5/1996 | (WO) . |

* cited by examiner

Primary Examiner—Todd E. Manahan
(74) Attorney, Agent, or Firm—Fitzpatrick, Cella, Harper & Scinto

(57) ABSTRACT

The invention relates to a medical or dental-medical instrument (1) for the material-removing working of body tissue or a substitute material, having an elongate handpiece (2), a holding device (4) arranged in the forward end region of the handpiece (2), and a tool (5) having a tool shaft (5a) and a tool body (5b) connected therewith, which is releasably connected with the handpiece (2) by means of the holding device (4), there being arranged in the handpiece (2) a vibration drive (6) for the tool (5), which transfers to the tool (5) high frequency oscillating movements, back and forth in at least one plane or orbital or three-dimensional, the tool body (5b) having an abrasive working surface (5c), the tool body (5b) being formed by means of a lamina (B), and the working surface (5c) being arranged at a narrow edge (21) of the lamina (B).

19 Claims, 4 Drawing Sheets

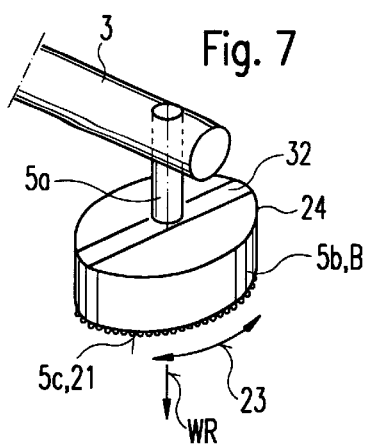
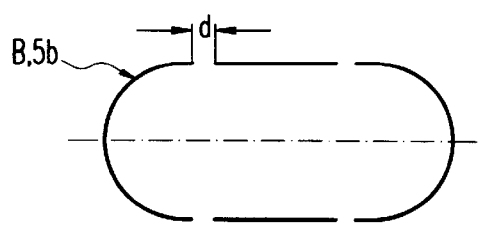
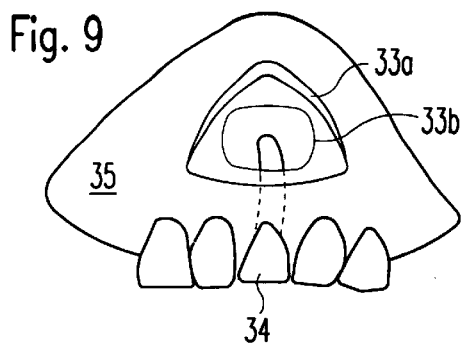
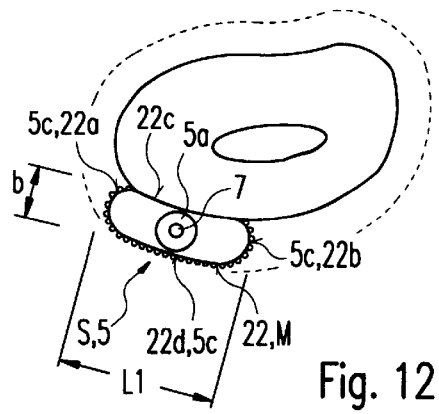
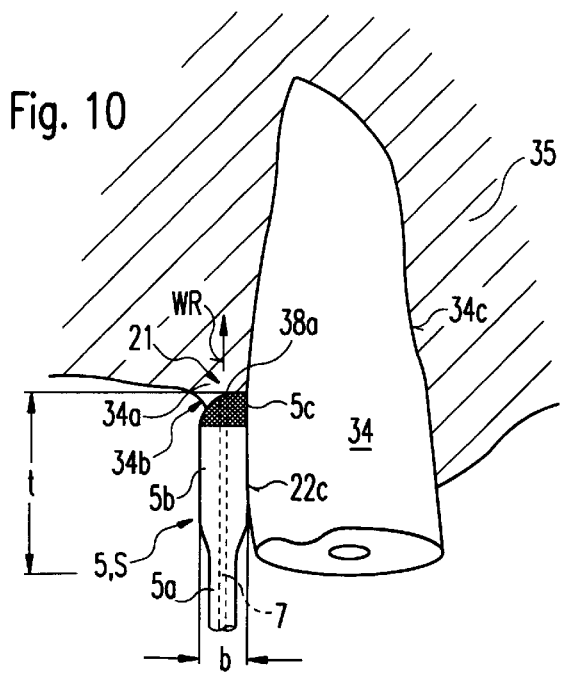
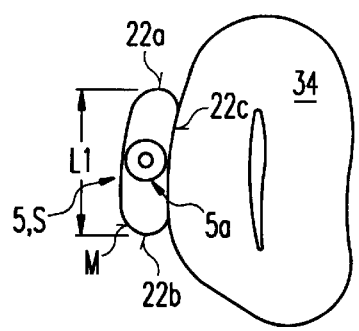

MEDICAL OR DENTAL-MEDICAL INSTRUMENT FOR MATERIAL-REMOVING WORKING OF BODY TISSUE AND TOOL FOR SUCH AN INSTRUMENT

BACKGROUND OF THE INVENTION

1. Field of the Invention

This invention relates to the material-removing working of hard or soft tissues of the human or animal body or artificial parts thereof; and more particularly it concerns novel tools and instruments for such working.

2. Description of the Related Art

For the material-removing working of hard or soft tissues of the human or animal body or artificial parts thereof, such as e.g. protheses, there are already known various instruments and associated tools. Here, there may be involved both tools for a surface treatment and also tools for the making of a cavity or parting-off tools. Basically, one can divide the working movements of a tool of the kind being considered and associated instruments with drives into three groups, namely rotational movements, longitudinal movements and oscillation movements. A rotation movement takes place with conventional drills or millers and with circular saws. Longitudinal movements are employed for surface working, such as is the case with files, whereby the surface working may take place in a cavity, e.g. in a root canal, or at an outer surface, e.g. at the surface of a tooth or bone. Combinations of the above-mentioned movements are also possible and have also already been proposed for instruments and tools for the preparation of tooth root canals. A particular working movement is an oscillating movement, which may involve both a longitudinal movement, an orbital movement in a plane, e.g. orbital movements along a circular or elliptical path, or a three-dimensional movement. Significant features of such an oscillation movement are a high frequency and small amplitude.

Instruments and tools of the last mentioned kind are described for medical purposes in WO 96/14024.

SUMMARY OF THE INVENTION

The object of the invention is to so configure an instrument and a tool of the kinds indicated in the introduction that its scope of use is extended.

This object is achieved by means of a handpiece which contains a vibrator, a tool holding shaft connected to be vibrated by the vibrator and having an end which extends out from the handpiece and a tool connected to be vibrated in a given direction by the shaft. The tool is formed as a lamina which has extensive side surfaces which are separated by a narrow abrasive working surface which extends along a line. The direction of the line is independent of the direction of vibration.

The instrument in accordance with the invention is distinguished in that it has a tool body in the form of a lamina, which has the working surface on the narrow edge. In contrast to the known configurations the tool in accordance with the invention carries out the material removing working on a thin or line-like strip, the thickness of which is predetermined by the thickness of the lamina. As a result of this, the tool is not only efficient, because long incisions can be carried out with relatively little swarf or debris produced, but it is also possible after carrying out an incision to carry out one or more incisions running transversely of the previous incision or incisions so that a part of the object to be worked can be cut out. Thereby, the invention is based on the insight that due to the relatively slight magnitude of amplitude of the oscillations the lamina of the tool can be sunk into the object to be worked without the functioning of the tool being substantially impaired or prevented as is the case with conventional stroke-movement saws, which cannot be sunk into the object to be worked because thereby the relatively large stroke of the saw blade is prevented and the saw becomes incapable of functioning. In contrast thereto, the instrument in accordance with the invention, because of the small oscillation magnitudes of the tool body or of the lamina, remains unaffected even when the tool body or the lamina is sunk into the material being worked. For this reason the tool in accordance with the invention is suitable not only for the parting-off of an object which is smaller than the length of the tool, as is usual in the case of saw, but the tool body or the lamina may be smaller than the dimensions of the object and can also be sunk into the object to be worked.

The invention also relates to a medical or dental-medical instrument for the material-removing working of recess openings for implants in a body tissue of the human or animal body.

Previously, it was known to produce the recess openings for implants by means of a rotating tool and to emplace implants of corresponding cross-sectional shape into the recess openings.

This known manner of proceeding is disadvantageous because on the one hand rotating tools tend to go awry during the material-removing working and furthermore due to rotating tools there is predetermined a relatively large cross-sectional size for the receiving hole and for the implant. Furthermore, a rotationally symmetric cross-sectional form is disadvantageous, or restrictive of the range of use, for an implant with regard to the anchoring of the implant and the firmness of the bedding in. The above-mentioned difficulties arise in particular when a receiving opening extends only partly into the available jaw bone, e.g. when it at the same time extends into the tooth root pocket of a former tooth. Elongate oval implant cross-sections, as they correspond to the natural tooth root, e.g. in the upper jaw front tooth region, are not possible with rotational preparations. Also, kidney-shaped cross-sections, such as appear in the lower jaw tooth region, cannot be prepared rotationally.

Thus, in relation to another aspect, the invention has the object of so configuring an instrument for the material removing working of a receiving opening in a body tissue or a substitute material for receiving an implant, that a simple positioning of the receiving opening and/or a stable seating for an implant is attained.

This object is achieved by means of the a handpiece inside of which a high frequency vibrator is arranged, a tool located outside the handpiece, and a holding device connecting the vibrator to the tool for vibrating same, wherein the tool has the shape of a spatula having an abrasive narrow edge which forms an abrasive working surface. With this instrument in accordance with the invention no rotational movements take place. The tool body of the tool has, on its narrow edge facing in the direction of working of the tool, an abrasive working surface which due to the vibration drive of the instrument is abrasively effective and thereby removes the tissue evenly in a material removing manner. In this way, the receiving hole can be positioned in a simple manner in an exactly fitting way. Since with the instrument in accordance with the invention no rotational movements take place, there can be realised also cross-sectional shapes which deviate from a rotationally symmetric cross-sectional shape. Thereby it is of particular advantage to arrange a flattened or elongate cross-sectional form longitudinally of the object. This arrangement is very space saving and furthermore leads to a stable embedding of the implant in the tissue. These advantages apply in particular for jaw implants in the region of which, with regard to the anatomically factors and the presence of nerve channels, little space is available. With an arrangement of a non-circular cross-sectional form of the receiving hole in the buccolingual direction there can thus be gained a significant amount of space. Of particular significance is the gain in anchoring surface in particular when the anatomical conditions do not permit a deep preparation.

The invention relates also a tool for an instrument in accordance with the invention, with regard to the advantages which can be achieved thereby, attention is directed to the above-described advantages.

The configurations in accordance with the invention are suitable for both hard and soft tissue such as bone or flesh or skin.

This invention, in its more specific aspects, involves features which lead to simple, economically manufacturable, reliably functioning and efficient configurations of compact construction of the instrument and/or tool. Further, features are contained therein which contribute to the stabilisation to the embedding of the implant and furthermore provide for simple and economical forms for the implant.

BRIEF DESCRIPTION OF THE DRAWINGS

Below, there will be described in more detail the invention and further advantages which can be achieved thereby with reference to preferred embodiments and simplified drawings, which show FIG. 1 a medical or dental-medical instrument in accordance with the invention, in side view;

FIG. 7 a tool in a further modified configuration, in perspective view;

FIG. 8 a tool in further modified configuration, in a view from above;

FIG. 9 an operative representation, with operative incisions, of tools in accordance with the present invention in the case of the preparation of a tooth root tip;

FIG. 10 the tool in accordance with the invention in a further modified configuration in a side view in operative position at a tooth of the upper jaw;

FIG. 11 the tool according to FIG. 10 in a view from above;

FIG. 12 a view corresponding to the sectional view according to FIG. 11, with a tool in a further modified configuration;

DETAILED DESCRIPTION OF THE PREFERRED EMBODIMENTS

Figure 1:
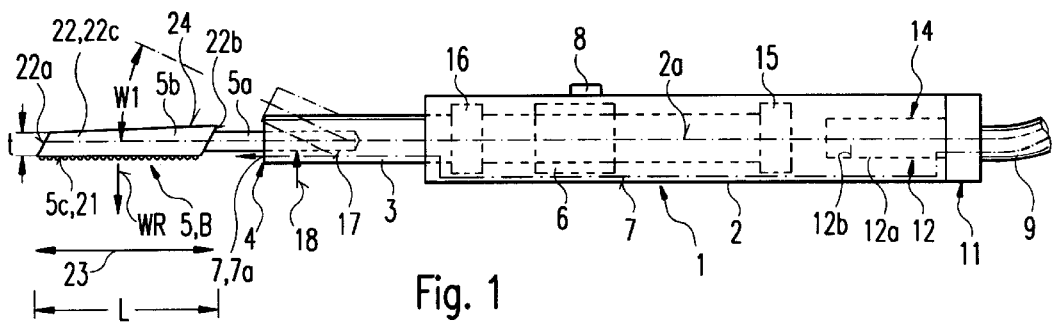

The instrument, generally designated 1 in FIG. 1, is suited in particular for bone, tooth and jaw working. The main elements of the instrument 1 are an elongate or rod-like handpiece 2, from the forward end of which a handpiece shaft 3 stands out, in the free end region of which there is arranged a holding device 4 in which a tool 5 having a tool shaft 5a and a tool body 5b standing out therefrom is releasably held, a vibration drive 6 for the handpiece shaft 3, which is arranged in the handpiece 2, and preferably also an electronic control device for increasing or decreasing the drive power, whereby the control device may be arranged in the instrument 1 or handpiece 2 or also remotely therefrom, e.g. at a non-illustrated control apparatus or a foot switch. Preferably, for the setting of the desired drive power, there is provided a setting member generally designated 8, which in the case of the present configuration is arranged on the outer surface of the handpiece 2 and is there displaceably mounted, but which ran also be arranged remote from the handpiece 2 or instrument 1. The handpiece 2 may be extend in a straight manner or it may also be a so-called angled piece having an angled gripping sleeve.

It is advantageous to provide an e.g. external, preferably sterile cooling medium supply, which may e.g. extend at the tool attachment. There may also be provided an internal cooling medium supply, which extends through attachment or stiffening elements for the tool.

The instrument 1 is connected with the control apparatus by means of a schematically illustrated flexible supply line 9 having a flexible supply tube, whereby there run in or on the supply line 9 one or more media lines 7 for the supply of the instrument 1 with energy and treatment and/or working media.

The present configuration, the instrument 1 consists of the handpiece 2 forming a forward instrument part and a connection piece 11, forming a rearward instrument part, which at its rear end is connected with the flexible supply line 9 and is releasably connected with the handpiece 2 by means of a quick-action coupling 12, in particular a plug-in or a screw coupling. The quick-action coupling 12 is preferably such a coupling which in the coupled condition permits a rotation of the handpiece 2 around its longitudinal middle axis 2a and thereby the passage of the medium or media present. With the present configuration there is provided a plug-in coupling having a cylindrical or stepped cylindrical coupling pin 12a and a coupling recess 12b which receives the coupling pin rotatably, whereby with the present exemplary embodiment the coupling pin 12a stands out forwardly from the connection piece 11 and the coupling recess 12b opens to the rear out of the handpiece 2. By means of a per se known releasable elastic safety device 14, which can in particular be manually overcome, there is prevented an unintended release of the plug-in coupling in the coupled condition. For a separation procedure, the safety device 14 effective with an elastically biased safety element can be overcome and released by ready manipulation.

Furthermore, it is advantageous to supply to the tool 5 in functional operation a preferably sterile fluid coolant or rinsing medium or a disinfectant medium. Such a medium can be delivered through the media line 7, which—passing through the quick-action coupling 12—may emerge e.g. at the forward end of the handpiece shaft 3 at an exit opening 7a directed at the treatment location, as is schematically illustrated in FIG. 1. Within the scope of the invention it is also possible and advantageous to let the medium line 7 so run longitudinally through the handpiece shaft 3, longitudinally through the tool shaft 5a and in the tool body 5b that it emerges at an exit opening located in the working surface 5c. It is also advantageous, if appropriate, to additionally arrange an exit opening in the broad face 22c or the broad face 22d, serving as bearing surface. By means of the coolant or rinsing medium supply device, generally designated with 7b, in particular also when with the tool 5 a blind hole preparation is made, swarf or debris can be rinsed away and removed out of the blind hole shaped preparation, whereby at the same time the outer surface of the tool is wet, cooled and rinsed, whereby the efficiency of the tool 5 is improved with a more gentle treatment for the patient. It is also possible to let a medium line 7 in the form of a hose line run externally of the handpiece 2 and to connect it with the exit opening 7a or with the handpiece shaft 3 and to allow the medium to reach the treatment location in the above-described way.

The handpiece shaft 3 is mounted in the handpiece 2 so that it can be elastically oscillated in all directions. For this purpose there may serve elastically yielding or compressible mounting parts, e.g. mounting rings, of which two are arranged at an axial spacing from one another and are schematically illustrated. The one bearing part 15 may be radially elastically yielding, whilst the preferably forward bearing part 16 is radially and axially yielding. Due to the elastically yielding configuration, the handpiece shaft 3 is returned by means of the elasticity of the bearing parts 15, 16 into a vibrational middle position in the rest state. The oscillation generator or vibration drive 6 generates high frequency short-stroke oscillations in the sense of a vibration with a frequency preferably lying in the sonic or ultrasonic range, whereby the oscillations or the amplitudes may be directed e.g. transversely and/or longitudinally of the handpiece shaft 3 or may be elliptically or circularly orbital, in each case in a plane or running with their direction changing in three dimensions. Orbital oscillations have proved to be advantageous. Because of the radially and axially elastically yielding mounting of the handpiece shaft 3 there arise in functional operation three-dimensional oscillations, so that the tool 5 is abrasively effective in all directions. The respective working direction WR of the tool 5, in which the latter is sunk into the material to be worked, is transverse, in particular at right angles, to the abrasive working surface 5c of the tool 5.

With the present exemplary embodiment, the vibration drive has a frequency of about 4 kHz to 8 kHz, preferably about 6 kHz, whereby in the vicinity of tool 5 there is provided an amplitude of the preferably three-dimensional oscillations, of about 0.05 mm to 0.2 mm, in particular 0.1 mm. Thereby, the control device may be so constituted that it makes possible a setting of the oscillation power in the above-mentioned range or also a setting above this range, so that if appropriate also considerably greater amplitudes can be set.

The instrument 1 in accordance with the invention is thus suited particularly well for different tools 5, which may be associated as a set of tools and which differ from one another due to different shapes and/or sizes and/or intended uses.

The holding device 4 has a plug-in hole 17 in the handpiece shaft 3 for the preferably cylindrical tool shaft 5a and has a locating device 18 for the tool shaft 5a which secures it in the plug-in hole 17 and may be rigid or so elastically yielding that in the case of a loading force effective at the tool 5 in the circumferential direction and/or axially being exceeded, the locating device 18 releases self-actingly, whereby damage or breaking of the tool 5 is avoided. For reasons of simplification, in the present exemplary embodiments, the locating device 18 is illustrated as an arrow. It may be a clamping screw radially screwed into the handpiece shaft 3 or an elastically biased rounding, which in each case engage into a recess (not shown) in the tool shaft 5a.

Figure 2:
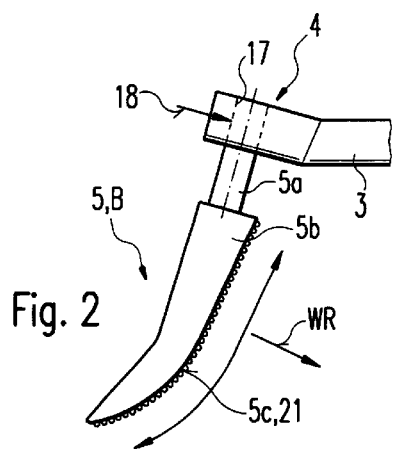
FIG. 2 an instrument shaft of a modified instrument having a holding device for a tool in a modified configuration.
Figure 3:
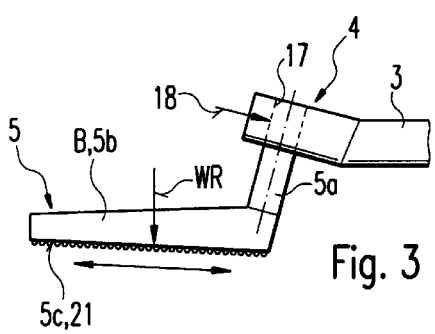
FIG. 3 a tool in modified configuration.
Figure 4:
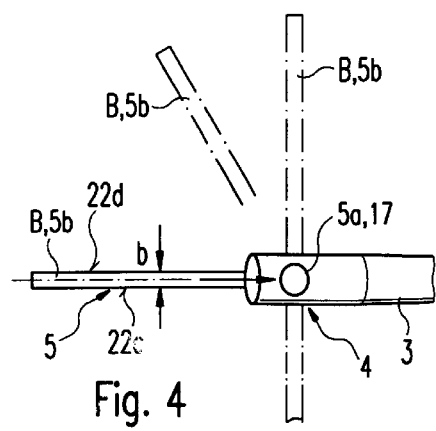
FIG. 4 the instrument shaft and the tool according to FIG. 3 in different working positions of the tool.

The handpiece shaft 3, preferably round in cross-section and in particular projecting axially from the handpiece 2, may extend straight, in accordance with FIG. 1, or be angled in its forward end region, e.g. by an angle W1 of about 5 to 30°, in particular about 15°. The plug-in hole 17 may be located axially (FIG. 1) or transversely, in particular at right angles (FIGS. 2, 3, 4), in the shaft 3, whereby the tool body 5b may be arranged with regard to the tool shaft 5a axially (FIGS. 1, 2) or projecting therefrom transversely, e.g. at right angles (FIGS. 3, 4). The handpiece 2 in accordance with the invention may also be so called angled handpiece.

The above-described configurations of the handpiece shaft 2 or angled piece shaft and/or of the tool 5 already make possible a multiplicity of tool positions with respect to the instrument 1 or the handpiece shaft 3, so that good accessability can be ensured even in difficult working positions at the body to be worked, e.g. in the mouth. As FIG. 4 clearly shows, the tool 5 can be rotatable around the longitudinal middle axis of the tool shaft 5a in steps or steplessly and be positioned settably in the holding device 4. By this means the instrument 1 or the tool 5 is further improved with regard to suitability for inaccessible working locations. Further, there is attained the advantage that one and the same instrument 1 is suitable for different working locations with different tools 5 and tool positions.

In accordance with a first aspect of the invention, the tool 5 has the form of a lamina B having a narrow edge 21 and two broad faces 22 extending therefrom, whereby the tool body 5b extends longitudinally in the longitudinal direction 23 of the narrow edge 21, as is the case with a saw blade. As working surface 5c, the narrow edge 21 is abrasively formed, whilst the rear surface 24, if appropriate forwardly convergent, the broad faces 22 and the remaining narrow edges 22a, 22b are smooth. The tool 5 is well suited, due to its lamina shape, for narrow incisions and for cutting or parting-off, whereby by reason of the relatively small width b of the narrow edge 21 or of the thickness of the tool 5, little working or parting debris arises. The width b may correspond that of a conventional saw blade, e.g. about 1 to 2 mm.

The working surface 5c is occupied by a multiplicity of point-like cutters, which are arranged distributed over the entire working surface 5c. Here, there may be involved geometrically defined or indeterminate cutters. Preferably, there are involved hard, adherent grains, in particular of diamond, feldspar or ceramics or tooth-like cutters of hard material, in particular hard metal (saw blade). Within the scope of the invention it is also possible to provide on the working surface 5c tooth-like cutters, e.g. as with a saw blade. The spacing of the cutters from one another is equal to or smaller than the amplitude of the vibration movements. By these means, the working surface 5c is, in vibration operation, an abrasively effective surface which machines an object to be worked, e.g. a bone, a model or a tooth, in a material-removing manner. Thereby, the tooth 5 behaves in principle as a saw blade, since it is—like a saw blade—moved oscillatingly parallel to its working surface 5c at the object to be worked. A significant difference of the present tool 5 consists in that the movement direction of the vibration movements is independent of the longitudinal direction 23 of the working surface 5c, when in the case of a linear oscillating movement this is directed parallel to the working surface 5c and in the case of an orbital oscillating movement the orbital plane is directed parallel to the working surface 5c. In the case of a three-dimensional oscillation movement, the extension of the working surface is completely independent. This can be explained in that due to its diamondisation or its point-like cutters, the working surface 5c is in the case of oscillating movements in one plane effective for cutting in all directions of this plane and in the case of a three-dimensional orbital oscillating movement is effective in any extension, since the three-dimensional oscillating movements due to their arc shape contain movement components which are directed at least partially approximately parallel to the working surface 5c and thus the working surface 5c is always effective in a scouring manner and thus effective for material removal.

Figure 6:
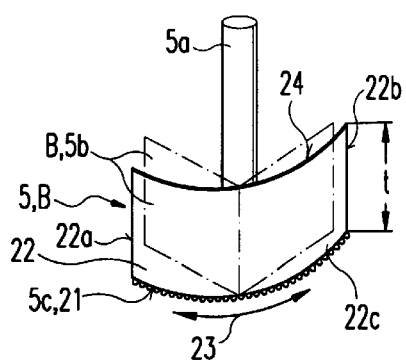
FIG. 6 the instrument shaft with a tool held therein, in perspective view from the front.

From this it follows that the tool 5 need not extend straight, in the longitudinal direction of the working surface 5c, but can deviate from this direction, e.g. in an angled shape, arc shape or annular shape, as FIGS. 6 to 8 show by way of example, as will be further described below.

It is to be emphasized that the tool 5 is also abrasively effective and capable of functioning when the oscillating movements are directed transversely to the broad faces 22. Since the amplitudes of the oscillating movements are relatively small there is available for the tool 5, in the cut clearance which forms, a sufficiently great play for movement that the tool can carry out the oscillating movements also when the main direction is directed transversely to the broad faces 22, on which the tissue of the cut clearance laterally bears. On the one hand this is due to the fact that the cut clearance arising from the oscillating movements is slightly greater than the width b of the working surface 5c and furthermore that the tissue is slightly yielding, in particular when the object to be worked is a bone or the tissue of a human or animal body.

Below, the configurations in accordance with the invention according to the remaining Figures will be described.

Figure 5:
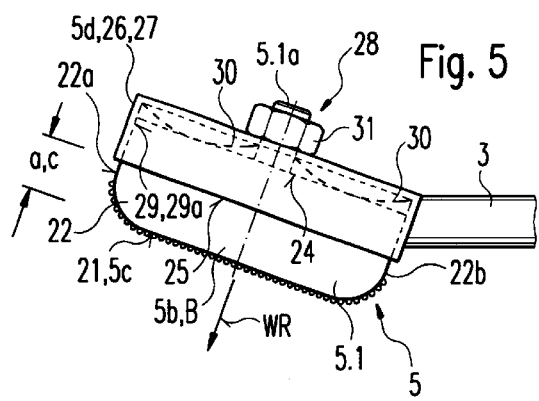
FIG. 5 a tool in modified configuration.

With the exemplary embodiment according to FIG. 5, in which the same or similar parts are provided with the same reference signs, there is associated with the tool 5 a depth stop 25 which extends approximately parallel to the working surface 5c and/or is located at a spacing a therefrom and upon meeting the object to be worked limits the working-in movement longitudinally of the working-in or effective direction WR extending transversely of the working surface 5c. The depth stop 25 may be formed by a frame-like setting, in particular a plug-in setting 26 into which a tool part 5.1 can be inserted. Such a plug-in setting 26 can be provided as a part 5d of the tool 5 or as adapter 27, whereby the part 5d or the adapter 27 has the mounting shaft 5a and can be held with this in the holding device 4.

Preferably, the spacing a and thus the working-in depth c determinable by means of the depth stop 25, can be made smaller and greater and be varied and set by means of a setting device 28. For this purpose, the part 5d or the adapter 27 has a guide 29 for the tool part 5.1 in which it is displaceable transversely of the working surface 5c. With the present configuration there is provided a diskshaped tool part 5.1 from the narrow rear surface 24 of which a tool shaft 5.1a projects, onto which a nut 31 can be screwed against a guide part 29a present and which is capable of adjusting and setting the tool part 5.1 longitudinally of the effective direction WR. With the present configuration, the guide part 29a is a narrow guide frame receiving a right-angled section of the tool 5.1 with slight play for movement, whereby spring elements 30, e.g. spring wires, are arranged between the tool part 5.1 and parts of the guide frame confronting it. As can be understood from FIG. 5, the guide 29 is, with reference to the longitudinal middle axis of the handpiece shaft 3, preferably arranged correspondingly tilted by the angle W1.

It is for reasons of lubrication of the guide 29 advantageous to so arrange the exit opening 7a or a continuing medium line 7 extending through the tool shaft 5.1a, that the treatment or cooling fluid enters the guide 29 in particularly from the rear, from which it can flow further to the working surface 5c, see flow arrows in FIG. 5. Here there may be involved a cooling medium supply device which, with regard to the handpiece, is arranged externally or is integral.

With the exemplary embodiments according to FIGS. 6 to 8 in which the same or similar parts are provided with the same reference signs, the tool body 5b is, with regard to the longitudinal direction 23 of its narrow edge 21 and working surface 5c shaped transversely of the broad faces 22 deviating from a straight line, e.g. arch or circular arc section shaped or angle shaped, as is schematically shown in FIG. 6 with solid lines and with chain lines. With this configuration, the tool body 5b is a lamina shaped strip which is correspondingly prismatically bowed or angled, has the working surface 5c at the narrow edge 21 and is connected with the tool shaft 5a at the back 24, preferably centrally. With this configuration, the working surface 5c extends correspondingly arc shaped or angle shaped whereby it may extend in a plane running transversely to the tool shaft 5a or may have a shape deviating from this plane. The remaining two narrow edges 22e, 22d may be formed parallel or wedge-shaped to one another or to the effective direction WR.

With the configuration according to FIG. 7, in which the same or similar parts are designated by the same reference signs, the tool body 5b is formed closed in the circumferential direction or tube or frame-shaped, whereby the illustration shows a tool body 5b whose strip or lamina is formed or bent hollow cylindrically. In similar manner, the tool body 5b, may have, seen longitudinally of the tool shaft 5a, a right-angled or triangular hollow cross-sectional form, if appropriate with rounded corners. The tool shaft 5a may thereby be arranged on the back 24 of the lamina away from the circumferential working surface 5c and thus eccentrically or on a transversely arranged spoke 32, which can also be realised with a configuration according to FIG. 6.

As FIG. 8 shows, the tool body 5b need not to be continuous in the circumferential direction, but it may consist of straight and/or curved sections or segments which may have a spacing d from one another extending in the circumferential direction. With a tool body 5b closed in the circumferential direction a hole can be worked in or cut in in one process and be removed by separation in its base region. With the configuration according to FIG. 8, the remaining webs in the region of the spacings d are to be parted-off by means of manual follow-up work. In the use of tool bodies 5b which are not closed in the circumferential direction, e.g. are formed angle-shaped or U-shaped, a section of the object to be worked which is to be removed can be worked and removed by cutting in the object in a plurality of stages and a corresponding displacement after each incision.

Furthermore, with the configurations according to FIGS. 6 to 8, it is possible and depending upon the particular case advantageous, to form the segment or ring or sleeve-shaped tool body 5b forwardly convergently or in the manner of a pyramid or truncated cone, whereby repositionable body parts, e.g. so-called bone flaps, can be worked and put back in place. FIG. 9 shows an above-described operation in the field of a tooth root tip resection, with which first a larger ring or angle cut 33a is worked in and the corresponding body part removed or folded away and then a smaller ring cut 33b is worked in the region of the tooth root tip of the tooth 34 present, and thus the root tip exposed.

With the configuration in accordance with the invention, the length of the tool body 5b, designated by L, can be formed greater than its depth t by a multiple thereof, as is shown e.g. in the above-described FIGS. 1 to 7, or the length L can correspond approximately to the depth t or be smaller than the depth t, whereby the tool body 5b attains the shape of a spatula S with broad faces 22 preferably developing parallel to one another and narrow edges 22a, 22b. The tool body 5b is preferably so adapted to the transverse dimensions of a tooth that it can be introduced between a tooth 34 and the associated gum 34a, e.g. in order to clean a tooth pocket 34b in part or all the way round, or by means of selective bone removal to extend a tooth receiving hole 34c in order e.g. in the case of a broken tooth to make the tooth root accessible to a pliers for the extraction of the tooth root, and by means of transmission of oscillations to loosen the remaining tooth root. With this configuration, one broad face 22, namely the broad face 22c towards the tooth 34, may be in the cross-section shown in FIG. 11 concavely rounded approximately in the shape of a section of a circular arc. The working surface 5c of the tool body 5b or spatula S—seen transversely to the longitudinal middle axis or broad face 22c of the spatula S—may be convexly rounded or—seen transversely to the narrow edge 22a, 22b—externally convexly rounded (see FIG. 10), whereby the roundings can run out at corners in the adjoining broad face 22c. These configurations are excellently suited for marginal bone moulding, whereby only the region of the narrow edge 21 of the spoon-shaped tool body 5b is abrasive, as is likewise shown in FIG. 10, and the spatula S is thus abrasive only at its forward end. Such a tool body 5b is more efficient if—as shown in FIG. 12—also the outer broad face 22d, opposed to the abutting broad face 22c, and the narrow edges 22a, 22b extending from the outer broad face in the circumferential direction, that is if also the rest of the outer surface M is abrasive in the above-described manner, whereby these narrow edges 22a, 22b are preferably convexly rounded and run out into the adjoining broad face 22c with a corner or at right angles, as has already been described for the forward end of the tool body 5b. Because of the smooth form of the abutting broad face 22c, a tooth 34 is unaffected; in any event it is only frictionally affected in a negligible manner.

Figure 13:
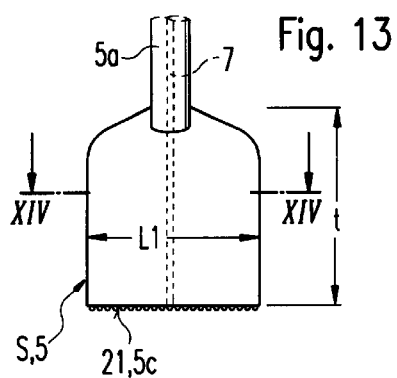
FIG. 13 a further modified tool with an instrument shaft, in a side view.
Figure 14:
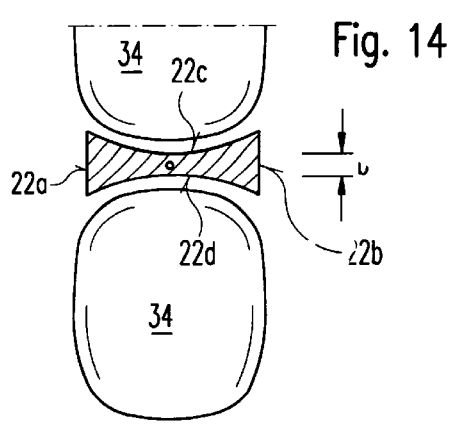
FIG. 14 the tool in the section XIV—XIV in FIG. 13 in a working position located between two teeth neighbouring one another.

A tool 5 in accordance with the invention in the above-described or a similar spatula shape is suitable also for paradontical surgical crown extensions, as is shown by FIGS. 13 and 14, in which the same or similar parts are provided with the same reference signs, the spatula-shaped tool body 5b has at both broad faces 22c, 22d concave or hollow cylindrical section shape, preferably smooth, bearing surfaces, whereby only the working surface 5c is to be abrasive and can be shaped to extend straight or somewhat convexly, in order to remove material of the gum 34a or also of the jaw bone 35 present in the region of a crown extension.

Figure 16:
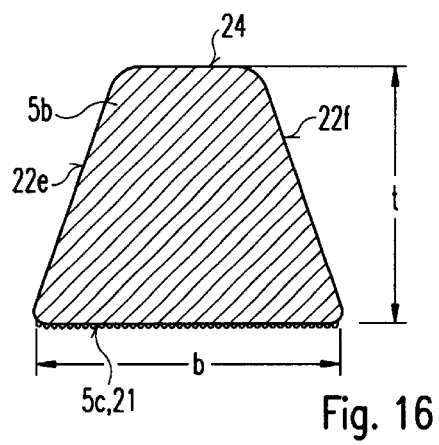
FIG. 16 the section XVI—XVI in FIG. 14.
Figure 17:
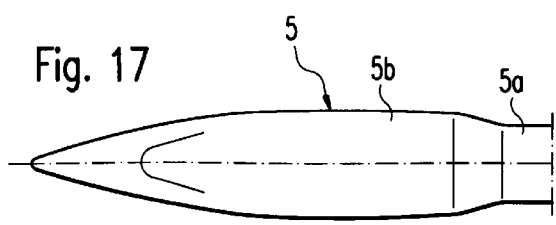
FIG. 17 a tool according to FIG. 15 and 16 in a view from above.
Figure 18:
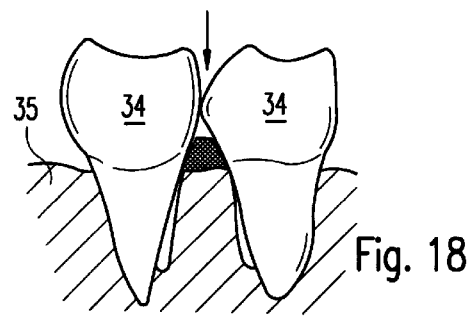
FIG. 18 the tool according to FIGS. 15 to 17 between two teeth of a row of teeth.

An alternative form of configuration, which is likewise suitable for paradontical surgical crown extensions, is illustrated in FIGS. 15 to 18. With this configuration, the tool 5 is, in the side view, formed correspondingly to FIG. 1. In accordance with FIG. 16, however, the cross-sectional shape differs in that the tool body 5b is formed substantially rod-shaped with a straight extending elongate working surface 5c, the width b of which corresponds approximately to the depth t, whereby the sides present to the rear 24 of the tool body 5b, present here not as broad faces but as normal side surfaces 22e, 22f may develop convergently or triangularly and the longitudinal edges are preferably rounded as is shown in FIG. 16. Furthermore, the width b may converge towards the forward end of the tool body 5b in the shape of a wedge or slightly rounded, as is shown in FIG. 17. FIG. 18 shows a location of use for the tool body 5b between two neighbouring teeth 34.

With known bone bed preparations with rotating tools it is only possible to prepare rotationally symmetric receiving openings for cylindrical, conical or screw-shaped implants. The invention is based on the insight that longitudinally of the arc of teeth elongate preparations are more favourable for anatomical reasons (jaw cavities, nerve channels) and that a spatula-shaped tool S in accordance with the present invention is very well suited for the working of such bone bed preparations. Due to the elongate cross-sectional shape, the tool 5 in accordance with the invention, and a bone bed preparation formed therewith, comply with the above-mentioned requirements resulting from the anatomical situation, whereby there is attained a shape and position of the bone bed preparation which is favourable for the arc-shape of the jaw 35 and nerve channels remain unaffected.

Figure 19:
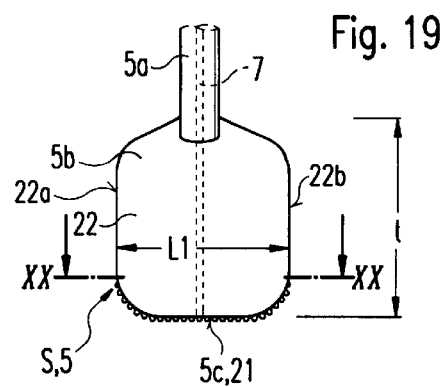
FIG. 19 a further modified tool, in a side view.

For this purpose there is particularly well suited a spatula-shaped or wedge-shaped tool 5 in accordance with FIG. 19 and following, in which the same or similar parts are provided with the same reference signs. The spatula-shape may, with regard to the dimension L1, be parallel or may taper in wedge shape towards the free or forward end. This configuration in accordance with the invention is with regard to particular aspects in accordance with the invention of particular advantage. A significant feature consists in that the spatula shape is elongate in cross-section, i.e. the length of the cross-section here designated L1 is greater than the width b of the cross-section, whereby the narrow edges 22a, 22b (FIG. 20) lying opposite to one another and/or broad faces 22 (FIG. 21) may be plane or convexly rounded, in particular cylinder section shaped or with regard to the narrow edges 22a, 22b semi-cylindrically rounded. An advantageous cross-sectional form is oval. Further, the tool body 5b may—seen longitudinally of its outer surface M—be curved around a centre of curvature lying externally of the cross-sectional shape, the radius of which is designated by R and preferably approximately corresponds to the radius of the jaw bone arc 35a, so that a lens-shaped or hollow cylindrical section shaped cross-sectional form is provided. That is, the broad faces 22 may be curved around a centre of curvature. The width b may be, with this configuration, about 2 to 12 mm, in particular about 4 or 6 to 8 mm, whereby an advantageous arrangement in the jaw bone is attained. The length L1 can be approximately adapted to the usual width dimension—running longitudinally of the jaw arc—of a tooth associated with the respective jaw arc region.

The narrow edge 21, extending transversely or at right angles to the outer surface M may have a flat or bulge-shaped or convexly rounded on all sides working surface 5c, whereby the outer surface M formed by the broad faces 22 and the narrow edges 22a, 22b may be smooth. It is, however, possible within the scope of the invention to provide that the outer surface M is also abrasive in the above-described sense.

The implant 37 may also manifest a corresponding cross-sectional shape.

Figure 20:
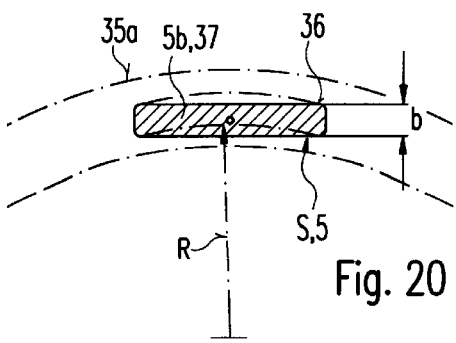
FIG. 20 the section XX—XX in FIG. 19.
Figure 15:
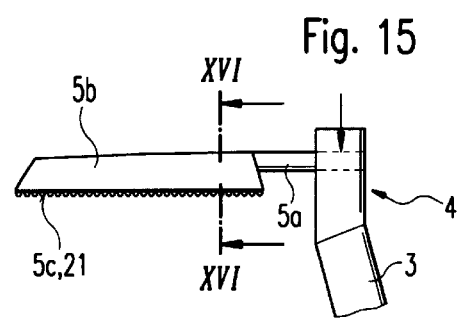
FIG. 15 an instrument shaft with a further modified tool, in side view.

In FIG. 20, the cross-sectional shape of the tool body 5b or of the implant 37 is illustrated in relation to a jaw bone arc 35a as a straight extending cross-sectional form and as a curvedly (indicated by chain lines) extending cross-sectional form. The working of the receiving opening 36 for an associated implant, which here has a plate-shaped or strip-shaped cross-sectional form, can be worked in one procedure with only the tool 5 in accordance with the invention, or the lateral ends of the receiving opening 36 can be prepared in advance by means of a rotating tool of corresponding cross-sectional size and then the intermediate region can be supplemented with a tool 5 in accordance with the invention, to e.g. a slit-shaped receiving opening cross-section.

Figure 21:
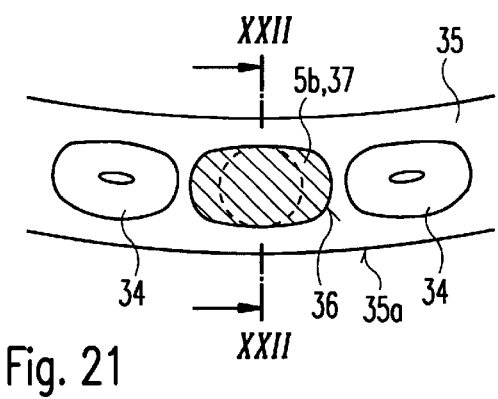
FIG. 21 the tool or an implant in cross-section in a position located in the jaw bone.
Figure 22:
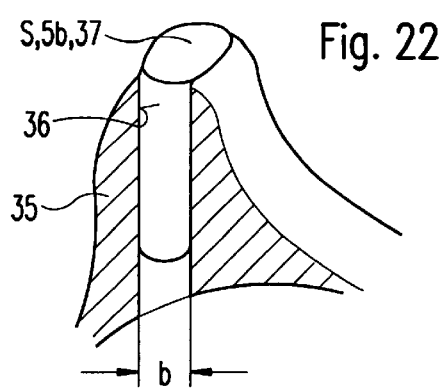
FIG. 22 the section XXII—XXII of FIG. 21, in a perspective illustration.

In FIG. 21, there is perspectively illustrated the convexly rounded cross-sectional form of the tool body 5b, or a corresponding implant 37, at both broad faces 22, in relation to the jaw tooth arc 35a. The configurations according to FIGS. 21 and 22 are suitable for the entire jaw, and particularly well suited for the front tooth region of the upper and/or lower jaw. FIG. 22 shows a perspective side view of the tool body 5, or the correspondingly shaped implant 37, emplaced in the jaw bone.

An above-described oval or lamina-like cross-sectional shape of the tool body 5b and/or of the implant 37 also provides an advantageous adaptation to the tooth root cross-sections, which in the buccolingual region are elongate oval, in particular in the front tooth region of the upper and lower jaw.

Figure 23:
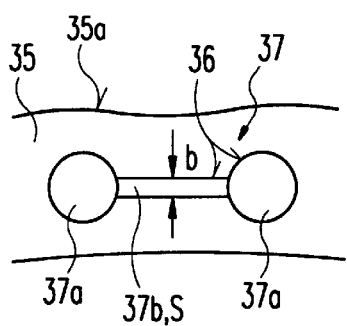
FIG. 23 a view corresponding to FIG. 21 in a modified configuration of the tool or the implant.

With the configuration according to FIG. 23, there is illustrated a receiving opening 36 in relation to the associated jaw tooth arc 35a, which receiving opening has the cross-sectional form of a double T for a correspondingly shaped implant 37, whereby the end cross-sectional enlargements 37a are larger than the width b of the web 37b of the implant 37 extending therebetween. With this cross-sectional form the end regions can likewise be worked by means of a rotating tool, dimensioned with corresponding size, whilst the region therebetween extending in a slit-shape can be worked by means of a spatula shaped tool 5 in accordance with the invention. It is also possible to form the tool body 5b with this double T-shaped cross-sectional form.

Figure 24:
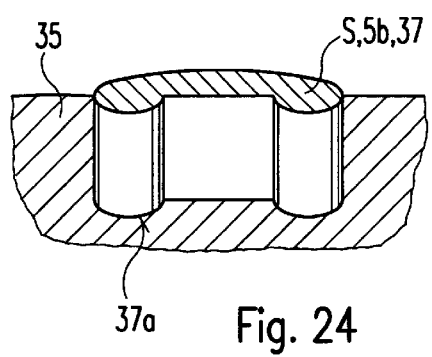
FIG. 24 a part of a tool or the implant in modified configuration, in perspective view from the side.

The modified cross-sectional shape of the tool body 5b, or of the implant 37, illustrated in FIG. 24 differs from the cross-sectional form according to FIG. 23 in that the web or slit-shaped receiving opening section between the end extensions 37a is not central but is offset towards one broad face, whereby an approximately C-shaped cross-sectional form is present. All cross-sectional forms according to FIGS. 19 to 24 have in common the feature that due to a cross-sectional form deviating from a rotationally symmetric cross-sectional shape a larger surface area is attained and the bone integration surface, and the load distribution in the case of loading when chewing, is improved.

The non-rotationally symmetric cross-sectional form in accordance with the invention can be prepared in a simple manner exactly or sufficiently exactly with a tool 5 in accordance with the invention, if appropriate after partial pre-preparation with a rotating tool.

Figure 25:
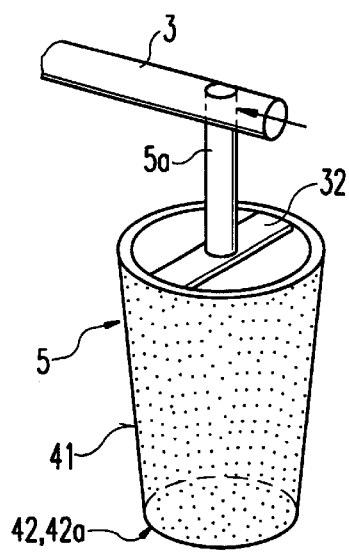
FIG. 25 a tool in further modified configuration, in perspective view from the side.

The configuration according to FIG. 25, in which the same or similar parts are provided with the same reference signs, shows a tool 5 the tool body 5b of which continuously tapers towards its forward end, in particularly cone or truncated cone shaped. In the case of the convergent shape, the end face and the outer surface are formed abrasively. This configuration is very well suited for the working of a receiving opening for an implant 37 in particular having a shape corresponding to the tool shape. The working can be pre-prepared with a rotating tool, the diameter of which may approximately correspond to the forward cross-sectional dimension of the convergent tool body 5b. It is also possible to form the tool body 5b tube-shaped. In this case, solely the outer surface and the forward edge need be abrasive. This configuration can also be realised with the exemplary embodiment according to FIG. 7. Correspondingly to any configuration the tool shaft 5a may also be attached to the tool body 5b.

Below, further advantages attainable by means of the invention will be summarised.

With known rotationally driven drills or millers for bone removal, e.g. in the case of removal of the wisdom teeth, because of the considerable toughness of the object to be worked, manually controlled guiding is only possible with difficulty, because the tool tends to run awry of an intended path. With the configuration in accordance with the invention, the tool can not only be applied in an aimed manner at the object to be worked, but also an insertion once made can be further developed in exact manner without particular manual effort having to be made in order to prevent running awry.

With a tool 5 in accordance with the invention, damage or injuries of neighbouring teeth are avoided, in particular in the case of marginal/interdental bone removal in parodontal surgical crown extensions.

In contrast to known bone saws, which are only functional in the direction of the backwards and forwards movement, with the tool in accordance with the invention, shapes of the tool body 5b deviating from the backwards and forward movement are also possible.

With the configurations according to FIGS. 10 to 14 and 19 and following, the tool shaft 5a may be arranged in the longitudinal direction of the spatula shape, i.e. approximately parallel to the working surface 5c, or be arranged transversely thereto, as FIGS. 10 to 14 show.

With all exemplary embodiments, the width b of the tool body 5b or lamina B or spatula S may be approximately 1 mm to 3 mm, preferably about 2 mm.

With the exemplary embodiment according to FIG. 25, in which the same or similar parts are provided with the same reference signs, the tool 5 has a cross-sectional form continuously tapering towards its free end, whereby the tool 5 may be of solid material or be maybe formed with a tube shape, so that it is internally hollow. The free end of the tool 5 may be rounded or cut off flat, so that in the case of a round cross-sectional shape the tool 5 has a truncated cone-shape. A cross-sectional form can, however, also have the above-described elongate cross-sectional shape. In all these cases, the tool 5 has a conically developing outer surface 41, which is formed abrasively in the above-described sense. If the tool is tube-shaped it is advantageous to apply to the preparation location, e.g. in the jaw bone, a pre-preparation, e.g. a bore, the cross-sectional size of which corresponds to the smaller cross-sectional size of the cone-shape. Thereby it is advantageous to form the ring-shaped end surface 42 likewise abrasively. When the tool 5 is of solid material or is closed at its free end and has a closed end face 42a, it is advantageous to form this end surface also abrasively.

What is claimed is:

1. Medical or dental instrument for the material-removal working of body tissue or a substitute material, said instrument comprising:

a handpiece which contains a vibrator;

a shaft connected to be vibrated by said vibrator, said shaft having an end which extends out from said handpiece; and a tool connected to be vibrated in a given direction by said shaft, said tool being formed as a lamina having smooth extensive side surfaces separated by a narrow abrasive working surface which extends along a line, the direction of said line being independent of said given direction of vibration.

2. Instrument according to claim 1, wherein, the tool body has no other abrasive working surface.

3. Instrument according to claim 1, wherein, the working surface is, in a longitudinal or transverse direction, thereof flat or convexly rounded.

4. Instrument according to claim 1, wherein, the lamina has a shape deviating transversely to its side surfaces.

5. Instrument according to claim 4, wherein, the shape is angle-shaped or rounded or curved.

6. Instrument according to claim 4, wherein, the shape is ring-form, whereby the cross-sectional shape of the tool is prismatic or and tapers towards its forward end.

7. Instrument according to claim 6, wherein, the cross-sectional shape of the ring is one of the group of shapes consisting of circular, curved, oval, triangular, rectangular, kidney shaped, and waisted kidney shape.

8. Instrument according to claim 1, characterised in that, the tool shaft is arranged longitudinally or transversely to said abrasive working surface.

9. Medical or dental instrument for the material-removal working of a receiving opening in a body tissue or a substitute material for receiving an implant, said instrument comprising:

a handpiece;

a high frequency vibrator arranged inside said handpiece;

a tool located outside said handpiece; and a holding device connecting said vibrator to said tool for vibrating same;

said tool having the shape of a spatula having an abrasive narrow edge which is curved and which forms an abrasive working surface.

10. Instrument according to claim 9, wherein, said spatula has an abrasive side surface which comprises a further working surface adjacent said working surface.

11. Instrument according to claim 9, wherein, said shape of said spatula has an elongate cross-section.

12. Instrument according to claim 9, wherein, said spatula shape has at least one curved broad face adjacent said narrow edge.

13. Instrument according to claim 9, wherein, said spatula shape has a cross-section which is thicker toward said narrow edge.

14. Instrument according to claim 1 or 9, further including, a stop on the handpiece or tool for limitation of working depth.

15. Instrument according to claim 14, wherein, the spacing of the stop from the working surface is adjustable by means of a setting device.

16. Instrument according to claim 1 or 9, further including, at least one media line extends longitudinally through the tool to an exit opening arranged in the working surface.

17. Instrument according to claim 1 or 9, wherein, said instrument includes a plurality of tools of different shapes or sizes.

18. Instrument according to claim 1 or 9, wherein, the vibrator is adjustable according to at least one of power, frequency and amplitude of vibration.

19. Instrument according to claim 1 or 9, wherein, the width of the tool is about 1 to 3 mm, and the dimension of the tool in a direction transverse to said working surface is about 3 to 10 mm.

* * * * *